United States Patent
Libbus et al.

(10) Patent No.: US 8,725,247 B2
(45) Date of Patent: May 13, 2014

(54) UNIDIRECTIONAL NEURAL STIMULATION SYSTEMS, DEVICES AND METHODS

(75) Inventors: Imad Libbus, St. Paul, MN (US); Avram Scheiner, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/532,469

(22) Filed: Jun. 25, 2012

(65) Prior Publication Data
US 2012/0265273 A1 Oct. 18, 2012

Related U.S. Application Data

(62) Division of application No. 11/695,189, filed on Apr. 2, 2007, now Pat. No. 8,224,436.

(51) Int. Cl.
*A61N 1/00* (2006.01)
(52) U.S. Cl.
USPC .................. 607/2; 607/62; 607/116; 607/118
(58) Field of Classification Search
USPC .................................. 607/2, 27, 44, 116, 118
See application file for complete search history.

(56) References Cited

U.S. PATENT DOCUMENTS

| | | | |
|---|---|---|---|
| 7,066,910 B2 | 6/2006 | Bauhahn et al. | |
| 7,072,720 B2 | 7/2006 | Puskas | |
| 7,277,761 B2 | 10/2007 | Shelchuk | |
| 7,292,890 B2 | 11/2007 | Whitehurst et al. | |
| 8,224,436 B2 | 7/2012 | Libbus et al. | |
| 2002/0099419 A1* | 7/2002 | Cohen et al. | 607/46 |
| 2003/0045909 A1* | 3/2003 | Gross et al. | 607/9 |
| 2003/0045914 A1 | 3/2003 | Cohen et al. | |
| 2003/0074039 A1 | 4/2003 | Puskas | |
| 2003/0236557 A1 | 12/2003 | Whitehurst et al. | |
| 2003/0236558 A1 | 12/2003 | Whitehurst et al. | |
| 2004/0015204 A1 | 1/2004 | Whitehurst et al. | |
| 2004/0098074 A1 | 5/2004 | Erickson et al. | |

(Continued)

FOREIGN PATENT DOCUMENTS

| | | |
|---|---|---|
| AU | 2008236864 B2 | 1/2012 |
| WO | WO2008123923 A2 | 10/2008 |

OTHER PUBLICATIONS

"Australian Application Serial No. 2011250875, Response filed Aug. 9, 2012 to Examiners First Report mailed Feb. 22, 2012", 22 pgs.

(Continued)

*Primary Examiner* — Carl H Layno
*Assistant Examiner* — Jennifer Ghand
(74) *Attorney, Agent, or Firm* — Schwegman Lundberg & Woessner, P.A.

(57) ABSTRACT

An embodiment relates to a method for delivering a unidirectional afferent nerve stimulation treatment. A test neural stimulation is delivered, and a physiologic response to the test neural stimulation is monitored. At least one neural stimulation parameter for the test neural stimulation is adjusted if the test neural stimulation does not elicit a desired physiologic response. If the test neural stimulation does elicit the desired physiologic response, at least one treatment parameter for a unidirectional afferent nerve stimulation is determined using the at least one neural stimulation parameter for the test neural stimulation that provided the desired physiologic response. The unidirectional afferent nerve stimulation is delivered using the at least one treatment parameter.

20 Claims, 11 Drawing Sheets

(56) References Cited

U.S. PATENT DOCUMENTS

| | | | |
|---|---|---|---|
| 2004/0172074 A1 | 9/2004 | Yoshihito | |
| 2004/0172085 A1 | 9/2004 | Knudson et al. | |
| 2004/0172094 A1 | 9/2004 | Cohen et al. | |
| 2004/0230255 A1* | 11/2004 | Dobak, III | 607/58 |
| 2004/0243182 A1 | 12/2004 | Cohen et al. | |
| 2004/0249422 A1* | 12/2004 | Gliner et al. | 607/58 |
| 2005/0131486 A1 | 6/2005 | Boveja et al. | |
| 2005/0143787 A1* | 6/2005 | Boveja et al. | 607/45 |
| 2005/0149131 A1 | 7/2005 | Libbus et al. | |
| 2006/0100668 A1 | 5/2006 | Ben-David et al. | |
| 2006/0116737 A1* | 6/2006 | Libbus | 607/44 |
| 2007/0021786 A1 | 1/2007 | Parnis et al. | |
| 2007/0191906 A1 | 8/2007 | Iyer et al. | |
| 2008/0109045 A1 | 5/2008 | Gross et al. | |
| 2008/0221640 A1 | 9/2008 | Overstreet et al. | |
| 2008/0234780 A1 | 9/2008 | Smith et al. | |
| 2008/0243196 A1 | 10/2008 | Libbus et al. | |
| 2010/0010556 A1* | 1/2010 | Zhao et al. | 607/17 |

OTHER PUBLICATIONS

"Chinese Application Serial No. 200880018561.7, Office Action mailed Mar. 25, 2013", 10 pgs.

"Chinese Application Serial No. 200880018561.7, Office Action mailed Sep. 30, 2013", With English Translation, 8 pgs.

"Chinese Application Serial No. 200880018561.7, Office Action mailed Jun. 5, 2012", With English Translation, 10 pgs.

"Chinese Application Serial No. 200880018561.7, Response filed Dec. 20, 2012 to Office Action mailed Jun. 5, 2012", With English Claims, 16 pgs.

"Japanese Application Serial No. 2010-502082, Office Action mailed Aug. 23, 2012", With English Translation, 5 pgs.

"Japanese Application Serial No. 2010-502082, Response filed Nov. 13, 2012 to Office Action mailed Aug. 23, 2012", With English Claims, 11 pgs.

U.S. Appl. No. 11/695,189, Advisory Action mailed, 3 pgs.

U.S. Appl. No. 11/695,189, Final Office Action mailed Jun. 17, 2010, 8 pgs.

U.S. Appl. No. 11/695,189, Non Final Office Action mailed Dec. 27, 2010, 10 pgs.

U.S. Appl. No. 11/695,189, Non-Final Office Action mailed Dec. 28, 2009, 8 Pgs.

U.S. Appl. No. 11/695,189, Notice of Allowance mailed Mar. 20, 2012, 8 pgs.

U.S. Appl. No. 11/695,189, Response filed Mar. 29, 2010 to Non Final Office Action mailed Dec. 28, 2009, 9 pgs.

U.S. Appl. No. 11/695,189, Response filed Sep. 17, 2010 to Final Office Action mailed Jun. 17, 2010, 10 pgs.

U.S. Appl. No. 11/695,189, Response filed Nov. 17, 2010 to Final Office Action mailed Jun. 17, 2010 and Advisory Action mailed Sep. 30, 2010, 12 pgs.

U.S. Appl. No. 11/695,189, Response filed Apr. 26, 2011 to Non Final Office Action mailed Dec. 27, 2010, 17 pgs.

U.S. Appl. No. 11/695,189, Response to Restriction Requirement mailed Oct. 30, 2009, 9 pgs.

U.S. Appl. No. 11/695,189, Restriction Requirement mailed Oct. 2, 2009 mailed Oct. 2, 2009, 9 pgs.

Australian Application Serial No. 2008236864, Examiner's Report No. 2 mailed Jun. 15, 2011, 3 pgs.

Australian Application Serial No. 2668236864, First Examiner Report mailed Aug. 27, 2010, 2 pgs.

Australian Application Serial No. 2008236864, Request to Amend a Complete Specification filed Apr. 27, 2011 in Response to Examiner's Report mailed Aug. 27, 2010, 22 pgs.

Australian Application Serial No. 2008236864, Response filed Aug. 17, 2011 to Office Action dated Jun. 15, 2011, 22 pgs.

Australian Application Serial No. 2011250875, Examiners First Report mailed Feb. 22, 2012, 2 pgs.

International Application Serial No. PCT/US2008/003683, International Search Report mailed Oct. 10, 2008, 3 pgs.

International Application Serial No. PCT/US2008/003683, Search Report mailed Oct. 10, 2008, 6 pgs.

International Application Serial No. PCT/US2008/003683, Written Opinion mailed Oct. 10, 2008, 7 pgs.

Japanese Application Serial No. 2010-502082, Office Action mailed Jan. 11, 2012, 9 pgs.

Japanese Application Serial No. 2010-502082, Response filed May 9, 2012 to Office Action mailed Jan. 11, 2012, English Claims Attached, 15 pgs.

Fallen, E. L., "Vagal afferent stimulation as a cardioprotective strategy? Introducing the concept", Ann Noninvasive Electrocardiol., 10(4), (Oct. 2005), 441-6.

Kamath, M. V., "Neurocardiac responses to vagoafferent electrostimulation in humans", Pacing Clin Electrophysiol., 15(10 Pt 2), (Oct. 1992), 1581-7.

* cited by examiner

UNIDIRECTIONAL NEURAL STIMULATION SYSTEMS, DEVICES AND METHODS

CLAIM OF PRIORITY

This application is a division of and claims the benefit of priority under 35 U.S.C. §120 to U.S. patent application Ser. No. 11/695,189, filed Apr. 2, 2007 now issued as U.S. Pat. No. 8,224,436, which is hereby incorporated by reference herein in its entirety.

TECHNICAL FIELD

This application relates generally to medical devices and, more particularly, to systems, devices and methods for delivering unidirectional neural stimulation.

BACKGROUND

Both experimental and clinical studies have demonstrated the potential adverse effect of sympathoexcitation in high risk patients with ischemia heart disease, as well as the potential for cardioprotection by programmed vagal activity. General vagal stimulation of the entire vagus nerve tends to decrease heart rate, lower respiration, and lower blood pressure.

Vagal afferent nerve stimulation through central medullary pathways increases cardiac vagal modulation to provide the benefits of central cardioinhibition, without adversely affecting heart rate, respiration or hemodynamics. However, typical closed-loop feedback control for vagal afferent nerve stimulation is difficult if the vagal afferent nerve stimulation does not have a significant effect on heart rate, respiration, or hemodynamics.

SUMMARY

An embodiment relates to a method for delivering a unidirectional afferent nerve stimulation treatment. A test neural stimulation is delivered, and a physiologic response to the test neural stimulation is monitored. At least one neural stimulation parameter for the test neural stimulation is adjusted if the test neural stimulation does not elicit a desired physiologic response. If the test neural stimulation does elicit the desired physiologic response, at least one treatment parameter for a unidirectional afferent nerve stimulation is determined using the at least one neural stimulation parameter for the test neural stimulation that provided the desired physiologic response. The unidirectional afferent nerve stimulation is delivered using the at least one treatment parameter.

An embodiment relates to a method for delivering a unidirectional afferent vagal stimulation treatment. Unidirectional efferent neural stimulation is delivered to a vagus nerve, and a physiologic response to the unidirectional efferent neural stimulation is monitored. At least one neural stimulation parameter for the unidirectional efferent neural stimulation is adjusted if the test neural stimulation does not elicit a desired physiologic response. If the unidirectional efferent neural stimulation does elicit the desired physiologic response, at least one treatment parameter for a unidirectional afferent nerve stimulation is determined using the at least one neural stimulation parameter for the unidirectional efferent neural stimulation that provided the desired physiologic response. The unidirectional afferent nerve stimulation is delivered using the at least one treatment neural stimulation parameter.

An embodiment relates to a method for delivering a unidirectional afferent nerve stimulation treatment, comprising delivering unidirectional afferent nerve stimulation to a target nerve using at least one electrode, interrupting delivery of the unidirectional afferent nerve stimulation to deliver a test neural stimulation to the target nerve using the at least one electrode, monitoring a physiologic response to the test neural stimulation, and declaring a failure of a neural stimulation pathway if the test neural stimulation does not elicit a desired physiologic response.

A system embodiment comprises a neural stimulator, a controller, and at least one sensor. The neural stimulator is adapted to generate neural stimulation signals for use in delivering neural stimulation. The controller is connected to the neural stimulator. The controller and the neural stimulator are adapted to generate a first neural stimulation signal for use in delivering unidirectional afferent neural stimulation to a target nerve for a neural stimulation therapy, and generate a second neural stimulation signal for use in delivering efferent neural stimulation to the target nerve. The sensor(s) is adapted to sense a physiologic response to the efferent neural stimulation of the target nerve. The controller is connected to the sensor(s), and is adapted to compare a sensed physiologic response to the efferent neural stimulation to a desired response, and adjust at least one efferent neural stimulation parameter for the second neural stimulation signal for use in delivering efferent neural stimulation that results in the desired physiologic response. The controller is also adapted to deliver the unidirectional afferent neural stimulation using afferent neural stimulation parameters deter using the at least one efferent neural stimulation parameter that provided the desired physiological response.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1:
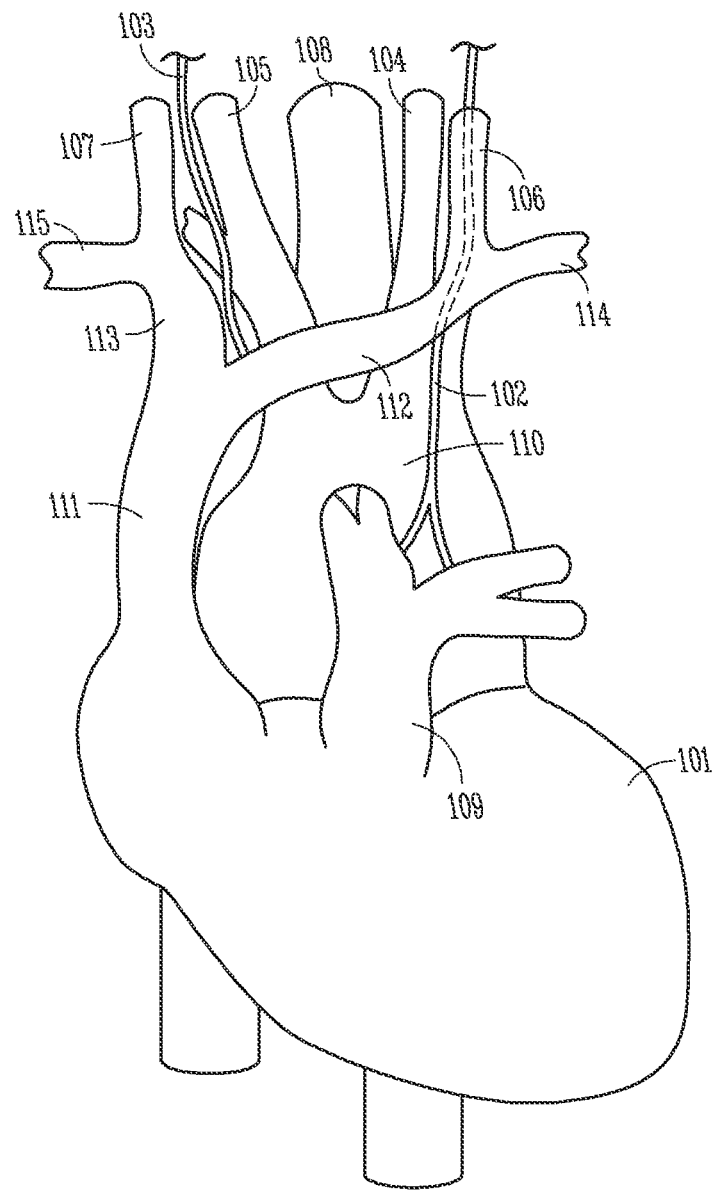
FIG. 1 illustrates a heart and anatomical features in a cervical region, including the left and right vagus nerves, the left and right carotid arteries, and the left and right internal jugular veins.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the fill scope of legal equivalents to which such claims are entitled.

The automatic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

The heart rate and force is increased when the sympathetic nervous system is stimulated, and is decreased when the sympathetic nervous system is inhibited (the parasympathetic nervous system is stimulated). An afferent nerve conveys impulses toward a nerve center. An efferent nerve conveys impulses away from a nerve center.

Stimulating the systematic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, increases digestion in the small intention, increases urine secretion, and contracts the wall and relaxes the sphincter of the bladder. The functions associated with the sympathetic and parasympathetic nervous systems are many and can be complexly integrated with each other.

Vagal modulation may be used to treat a variety of cardiovascular disorders, including heart failure, post-MI remodeling, and hypertension. These conditions are briefly described below.

Heart failure refers to a clinical syndrome in which cardiac function causes a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease.

Hypertension is a cause of heart disease and other related cardiac co-morbidities. Hypertension occurs when blood vessels constrict. As a result, the heart works harder to maintain flow at a higher blood pressure, which can contribute to heart failure. Hypertension generally relates to high blood pressure, such as a transitory or sustained elevation of systemic arterial blood pressure to a level that is likely to induce cardiovascular damage or other adverse consequences. Hypertension has been arbitrarily defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease.

Cardiac remodeling refers to a complex remodeling process of the ventricles that involves structural, biochemical, neurohormonal, and electrophysiologic factors, which can result following a myocardial infarction (MI) or other cause of decreased cardiac output. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. It is the combination of hemodynamic, sympathetic nervous system and hormonal alterations (such as presence or absence of angiotensin converting enzyme (ACE) activity) that ultimately account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

General stimulation of the vagus nerve to treat heart failure, post-MI remodeling, and hypertension, may reduce heart rate, blood pressure or have other physiologic effects. In clinical studies, electrical stimulation of vagal afferent fibers elicits dramatic and reproducible sustained shifts in the heart rate power spectrum toward enhanced vagal modulation. Because stimulation is limited to the afferent fibers, there is no change in mean heart rate, blood pressure, or respiratory frequency. Thus, afferent vagal stimulation may achieve vagal modulation without unnecessary physiological side effects.

Various embodiments described herein provide cardiac therapy via unidirectional afferent stimulation of a neural target, such as unidirectional vagal afferent stimulation. The present subject matter can be used to provide vagal stimulation for the treatment of cardiovascular disorders such as heart failure, post-MI remodeling, hypertension, and the like. The present subject matter can also be used to provide afferent vagal stimulation for other physiological disorders amenable to vagal stimulation treatments such as epilepsy, depression, pain, migraines, obesity, eating disorders, cardiac rhythm management, and the like.

Various embodiments provide an implantable stimulator to provide cardiac therapy via unidirectional afferent stimulation, allowing for vagal modulation through central pathways without adversely affecting heart rate, respiration or hemodynamics. Various stimulator embodiments are adapted to switch between unidirectional afferent stimulation to provide neural stimulation treatment, and unidirectional efferent stimulation to provide closed-loop feedback control useful for titrating the neural stimulation treatment, and is also useful for verifying the integrity of the neural stimulation pathway.

The neural stimulation device operates in a treatment mode and in a titration mode. Afferent stimulation is delivered in the "treatment mode". The device temporarily switches to the "titration mode" to deliver efferent stimulation to elicit measurable physiological effects, such as heart rate change or laryngeal vibration. The measurable physiological effects of the efferent stimulation allow the stimulator to verify lead integrity and titrate the stimulation intensity by adjusting one or more stimulation parameters(s), such as amplitude, frequency, duty cycle, and the like. The titrated stimulation parameters for the efferent stimulation is then used to deliver the affrent stimulation. Various embodiments switch between modes in response to a device interrogation by a physician or caregiver. Various embodiments automatically switch between modes on a programmed schedule. The schedule may provide for periodic switches between modes (hourly, daily, etc.).

In an embodiment, the neural stimulator is adapted to electronically switch between two or more of the following modes: unidirectional afferent stimulation, unidirectional efferent stimulation, and bidirectional stimulation. The present subject matter can be used to check for lead continuity and/or nerve recruitment. Neural stimulation may be delivered to the left or right vagal nerve, or both. If stimulation is delivered to both nerve trunks, the stimulator would have the capability of independently modulating the stimulation mode on each side.

A stimulator embodiment delivers afferent vagal stimulation using a lead positioned to provide direct stimulation of the vagus nerve in the cervical region. Some embodiments provide stimulation through a cuff placed around the nerve. The nerve cuff would be designed to provide unidirectional afferent stimulation by stimulating the nerve while blocking propagation in the efferent direction. This may be accomplished with a tripolar lead with an appropriate stimulation waveform. Some embodiments provide stimulation using a lead positioned proximal to the nerve, such as a transvascular lead placed in an adjacent vessel like the internal jugular vein. Unidirectional stimulation may be provided a variety of ways.

FIG. 1 illustrates a heart 101 and anatomical features in a cervical region, including the left and right vagus nerves 102 and 103, the left and right carotid arteries 104 and 105, and the left and right internal jugular veins 106 and 107. Also illustrated in FIG. 1 are the trachea 108, pulmonary artery 109, aorta 110, superior vena cava 111, the left and right innominate veins 112 and 113 (also referred to as brachiocephalic veins), and the left and right subclavian veins 114 and 115. Some embodiments transvascularly stimulate a desired neural target such as the vagus nerve. Those of ordinary skill in the art, upon reading and comprehending this disclosure, would understand how to transvascularly stimulate the neural target using vessels such as the internal jugular veins to access the neural target.

Figure 2:
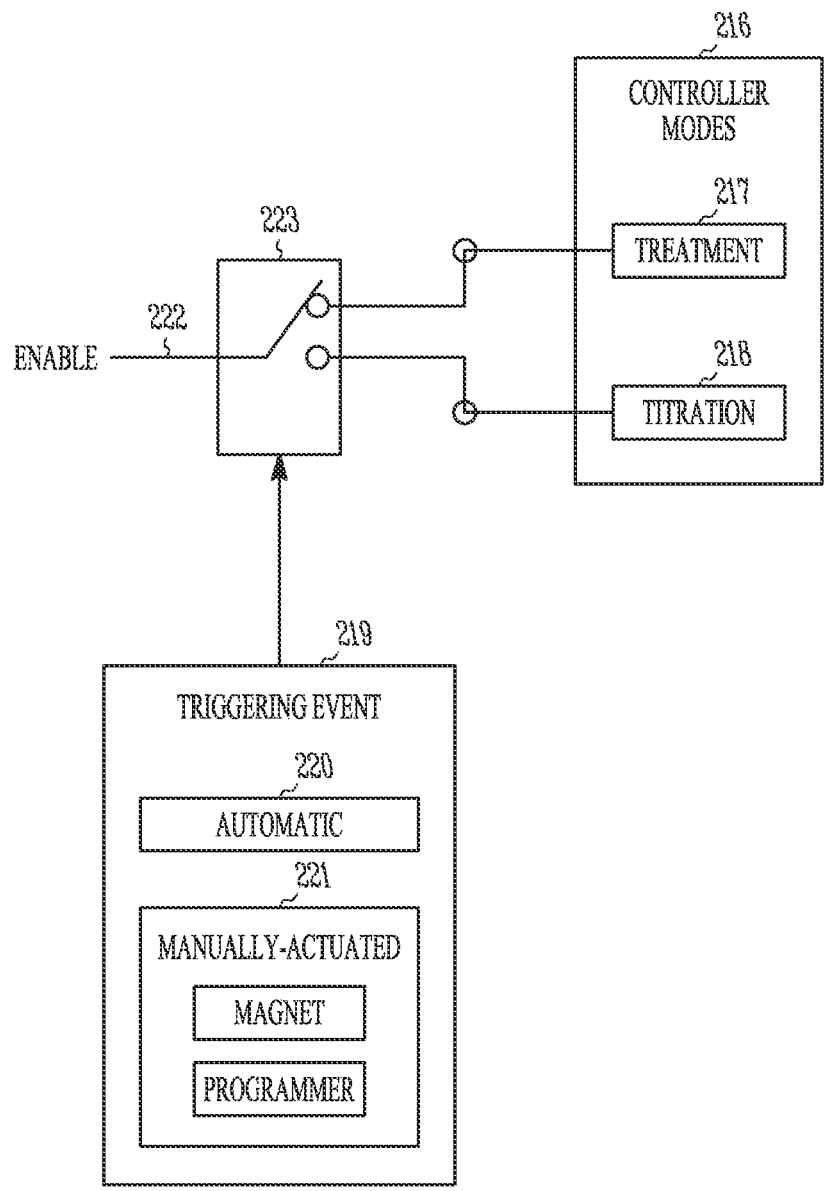
FIG. 2 illustrates an embodiment of a responsive relationship of an implantable medical device (IMD) controller to a triggering event.

FIG. 2 illustrates an embodiment of a responsive relationship of an implantable medical device (IMD) controller to a triggering event. The illustration includes a controller 216 adapted to operate the IMD in a treatment mode 217, a titration mode 218. The illustration further includes a representation of a triggering event 219, which can be an automatic event 220 and/or a manually-actuated event 221 such as a magnet moved proximate to a reed switch or a manually-actuated programmer. Examples of automatic triggering events include a detected device event change such as a detected possible electrode failure and a detected possible lead failure, such as may be detected by sensing a change in impedance or current. Automatic triggering events can also include a detected physiologic change such as a detected change in heart rate, a detected arrhythmia, a detected change in a respiratory rate, a detected change in neural traffic, a detected change in blood pressure, and a detected change in activity. Automatic triggering events can also be based on a timer or clock, such as a device with a controller and timer adapted to follow a schedule when switching modes. The illustration also includes an enable signal 222 connected to the controller to enable a mode of operation via a switch 223. The triggering event is adapted to control the switch 223 to selectively enable a mode of operation by the controller 216. The illustrated responsive relationship can be performed in hardware, software, or a combination thereof.

Figure 3:
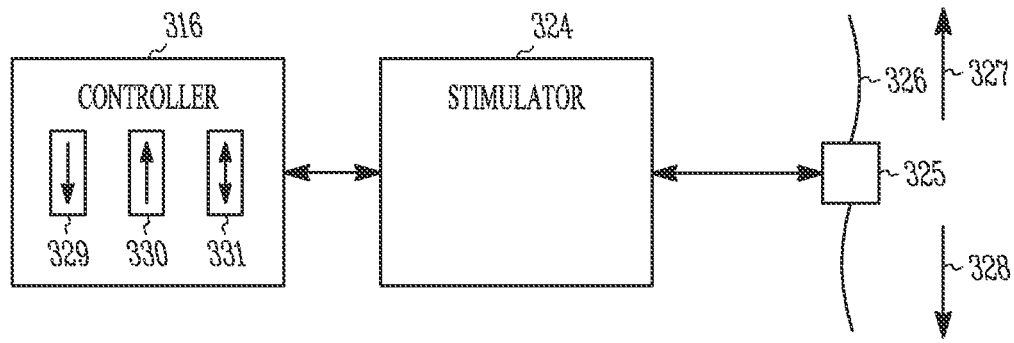
FIG. 3 illustrates a controller, a stimulator and an electrode system for use in stimulating a nerve, according to various embodiments.

FIG. 3 illustrates a con roller 316, a stimulator 324 and an electrode system 325 for use in stimulating a nerve 326, according to various embodiments. The illustrated electrode system cooperates with the stimulator and the controller to provide unidirectional stimulation in a first direction, such as an afferent direction illustrated by arrow 327. Some embodiments provide unidirectional neural stimulation in an opposing second direction, such as an efferent direction illustrated by arrow 328, and some embodiments provide bidirectional neural stimulation with action potentials in both the afferent and efferent directions. The illustrated controller 316 is adapted to control the neural stimulator 324 to deliver the appropriate stimulation through the electrode system 325 to provide the unidirectional afferent stimulation 329, the unidirectional efferent stimulation 330, and bidirectional stimulation 331.

Generally, an electrically stimulated axon produces action potentials that propagate in its normal direction of travel, and also in the opposite direction of its normal direction of travel. Thus, in a normally afferent neural pathway, an electrical stimulation generally produces action potentials that propagate in both the afferent direction and the efferent direction.

Those of ordinary skill in the art will appreciate that there have been a number of proposals to deliver unidirectional neural stimulation. Since the neural stimulation induces action potentials in both directions, some of these proposals to deliver neural stimulation involve blocking or inhibiting the action potential from traveling in the undesired direction. Examples of unidirectional nerve stimulation protocols involve blocking propagation of action potentials in one of the directions include, for example, neural stimulation with anodal blocking and neural stimulation with high-frequency blocking. Blocking the action potential can involve hyperpolarizing a portion of the axon membrane to prevent the action potential from passing through that portion of the axon membrane. The axon potential continues in the other direction through a depolarized portion of the axon membrane, thus providing unidirectional stimulation. Anodal blocking may be realized by using a cathodal current to depolarize the axon membrane and generate action potentials in opposing directions, and using a high anodal current to hyperpolarize the portion of the axon membrane to prevent the action potential from passing that hyperpolarized portion in a first direction, while allowing the action potential to proceed in an opposite second direction. The electrical signals used to generate the cathodal and anodal current can be timed in a manner to deliver the desired anodal current at a time determined to block the action potential. Different neural pathways allow action potentials to travel at different speeds, such that an action potential on one neural pathway travels at a different speed than an action potential on another neural pathway. The timing of the electrical signals can be adjusted to accommodate the different speeds of the propagation for the different neural pathways.

Figure 4:
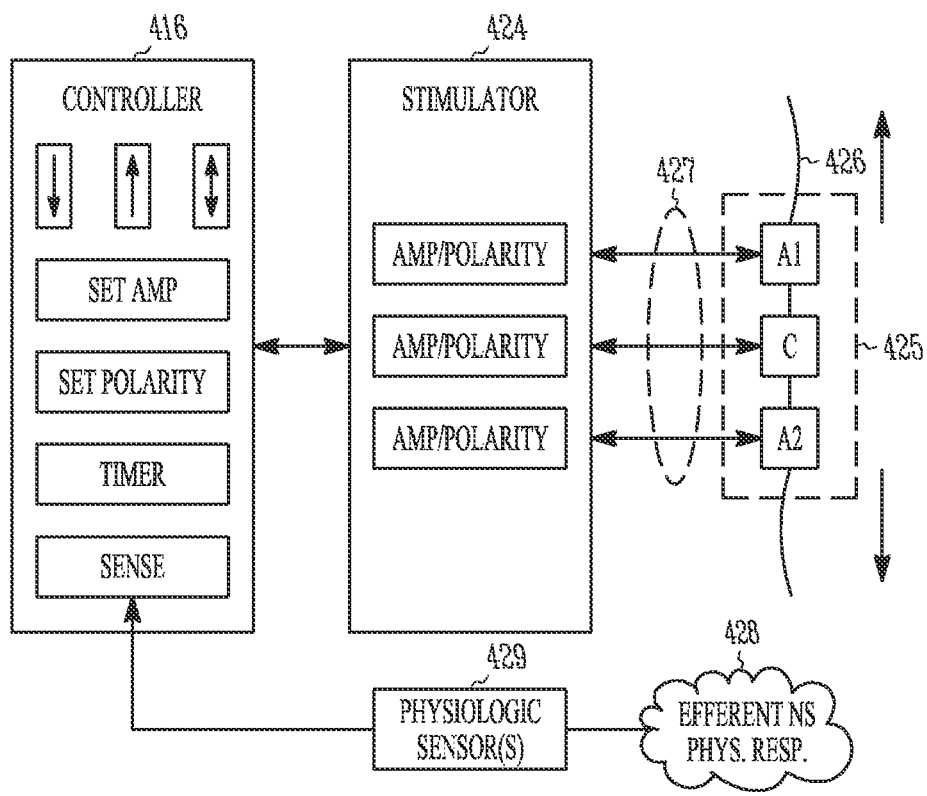
FIG. 4 illustrates a controller, a stimulator and a tripolar electrode system for use in stimulating a nerve, according to various embodiments.

FIG. 4 illustrates a controller 416, a stimulator 424 and a tripolar electrode system 425 for use in stimulating a nerve 426, according to various embodiments. The figure illustrates three stimulation channels between the stimulator and the electrodes. These stimulation channels can be incorporated in one lead, as illustrated by the line 427. The illustrated stimulator is adapted to generate a stimulation signal, that includes both an amplitude and polarity, for each channel. These stimulation signals generate potential differences between the electrodes (C, A1, A2), to provide the desired cathodal current in the cathodal electrode (C), and also to provide the desired anodal currents between the first and second anodal electrodes (A1 and A2). The illustrated controller 416 includes modules for setting the amplitude and polarity for the channel stimulation signals. The illustrated controller further includes a timer for use in timing the neural stimulation and the neural blocking. The timer can also be used to control scheduled therapy.

The illustrated tripolar electrode assembly includes a cathode electrode (C) positioned between first and second anodal electrodes (A1 and A2). A cathodal current can be driven through the cathodal electrode (C). The cathodal current in the cathodal electrode (C) is ideally the sum of the anodal currents in the anodal electrodes (A1 and A2).

In order to allow unidirectional propagation, the tripolar electrode assembly provides asymmetrical anodal current. One end has anodal current of sufficient magnitude to block propagation, and the other end has anodal current of sufficient magnitude to allow propagation. This asymmetry can be achieved in a number of ways. For example, some embodiments selectively increase decrease the resistance in one or both of the current pathways to selectively control the anodal current. For example, if the potential difference between an anode and the cathode remains the same, increasing a series resistance in the current pathway to one anode reduces the anodal current for that anode. The highest current density is under the cathode, the next highest is in the lower resistance anode (blocking neural propagation) and the lowest current density will be in the higher resistance electrode (allowing neural propagation). Some embodiments achieve the asymmetry by selectively controlling the potential between the cathode and anodes. An appropriate potential difference is applied between the cathodal electrode (C) and each of the anodal electrodes (A1 and A2) to provide more anodal current through one of the anodal electrodes (e.g. anode A2) than the other (e.g. anode A1). The higher anodal current hyperpolarizes the axon membrane, thus blocking the action potential from passing the anode (e.g. A1) with the high anodal current. The lower anodal current through the other anodal electrode (e.g. A1) depolarizes the axon to respond to an action potential, allowing the axon membrane to pass the action potential past the other anode (e.g. A1) to provide unidirectional afferent stimulation. Various embodiments of the present subject matter use one tripolar electrode assembly, and controls the amplitude, polarity and timing of the stimulation pulses to generate the desired cathodal and anodal currents to provide the desired unidirectional stimulation of the target nerve.

As provided above, the unidirectional efferent stimulation has more pronounced physiologic effect, illustrated by the efferent neural stimulation physiological response cloud, 428, than the unidirectional afferent stimulation, as the unidirectional afferent stimulation is mediated by the central nervous system. The present subject matter uses sensor(s) 429 to monitor the physiologic response to the efferent neural stimulation, and adjusts the stimulation parameters of the efferent stimulation accordingly to achieve a desired physiologic response. Examples of sensors include sensors of blood pressure, heart rate, respiration, and laryngeal vibrations. Any sensor of any physiological response to the efferent stimulation may be used. The controller uses the parameters that achieve the desired response to the efferent stimulation to determine the neural stimulation parameters for the afferent stimulation. Upon identifying the desired neural stimulation parameters in the efferent direction, various embodiments of the present subject matter switch the stimulation parameters associated with anodal electrodes (A1 and A2) to provide the desired unidirectional stimulation. For example, the stimulation parameters of the first and second anodes can be adjusted such that a first anodal current associated with the first anode during the efferent stimulation is approximately the second anodal current associated with the second anode during the afferent stimulation, and the second anodal current associated with the second anode during efferent stimulation is approximately the first anodal current associated with the first anode during the afferent stimulation. Various algorithms can be used to set the efferent neural stimulation parameter(s) based on or as a function of the effective afferent neural stimulation parameter using known relations between the afferent and efferent stimulation.

Figure 5:
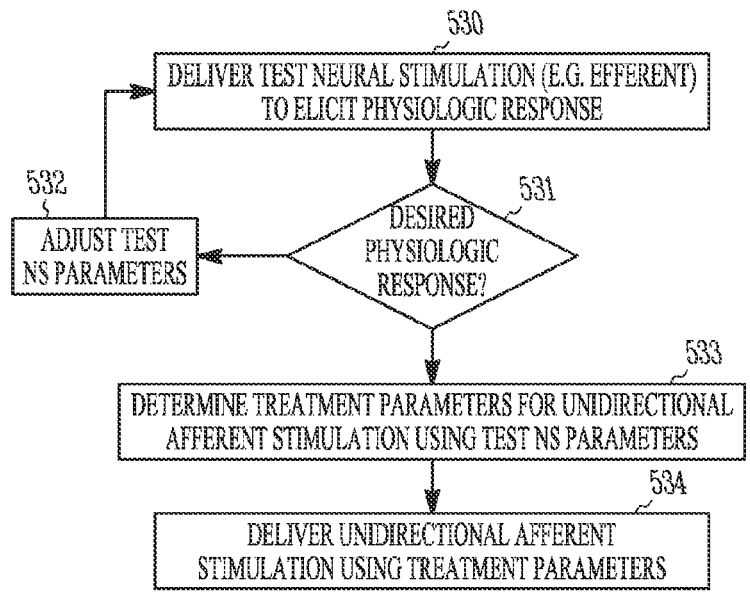
FIG. 5 illustrates a method for delivering a unidirectional, afferent neural stimulation treatment, according to various embodiments.

FIG. 5 illustrates a method for delivering a unidirectional, afferent neural stimulation treatment, according to various embodiments. At 530, a test neural stimulation is delivered to elicit a physiologic response. The test neural stimulation is delivered through an electrode system. In various embodiments, the test neural stimulation includes a bidirectional neural stimulation that includes both an afferent and efferent component. Some embodiments deliver the test neural stimulation as a unidirectional efferent neural stimulation. At 531, it is determined whether the test neural stimulation provides a desired physiologic response, such as may be determined using sensors to monitor for the expected or desired response. Examples include sensing heart rate, blood pressure, respiration, laryngeal vibrations, or various combinations thereof in response to efferent vagal stimulation. If the desired physiologic response is not realized by the test neural stimulation, the process proceeds to 532 to adjust at least one test neural stimulation parameter, such as amplitude, frequency, duty cycle, and the like, and the test neural stimulation is delivered again at 530 with the revised test neural stimulation parameters. If the desired physiologic response is realized, the process proceeds from 531 to 533 to use the current test neural stimulation parameters to determine the treatment parameters for the unidirectional afferent stimulation. In some embodiments, the same parameters are used to stimulate the target nerve, except that the stimulation is applied in a manner to provide unidirectional afferent stimulation. Some embodiment use a predetermined relationship between the afferent and efferent neural stimulation to derive or otherwise determine the treatment parameters for the unidirectional afferent stimulation based on the test parameters from the afferent stimulation. At 534, the unidirectional afferent stimulation treatment is delivered using the treatment parameters determined at 533. Some embodiments use the same electrode system to deliver both the test and the treatment stimulation.

In addition to in as alternative to adjusting the neural stimulation parameters if the desired response is not realized, some embodiments declare a failure of a neural stimulation pathway if the test neural stimulation does not elicit a desired physiologic response. This declared failure is communicated to a physician and/or patient, allowing the physician and/or patient to take remedial measures and not rely on the continued afferent stimulation treatment.

Figure 6:
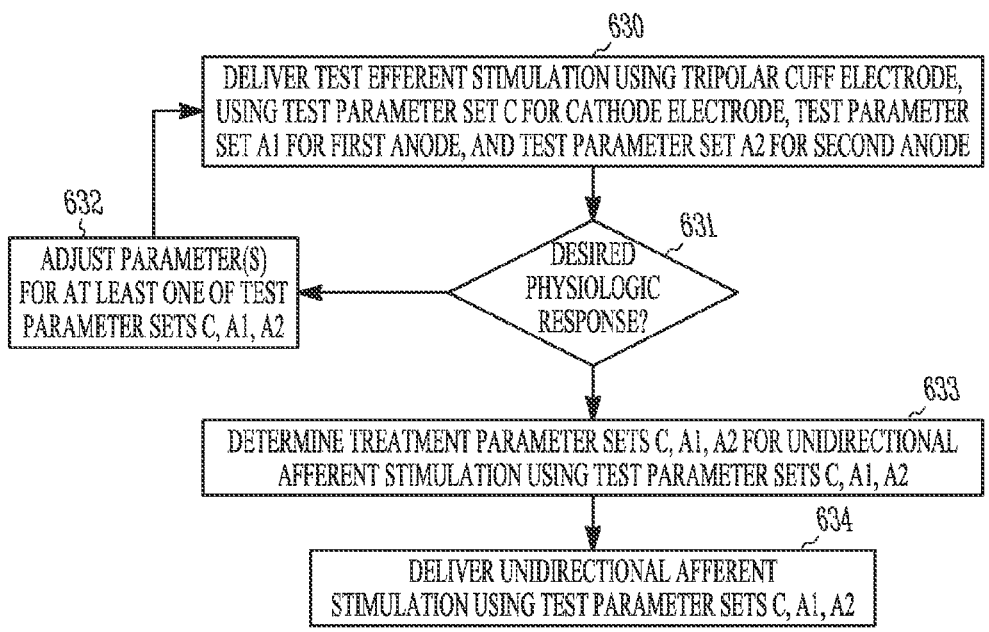
FIG. 6 illustrates a method for delivering a unidirectional, afferent neural stimulation treatment using a tripolar electrode, according to various embodiments.

FIG. 6 illustrates a method for delivering a unidirectional, afferent neural stimulation treatment using a tripolar electrode, according to various embodiments. At 630, a test efferent stimulation signal is delivered using a tripolar cuff electrode. The test efferent stimulation uses a test parameter set C for a cathode, a test parameter set A1 for a first anode, and a test parameter set A2 for a second anode. Each of the test parameter sets A1, A2, and C include stimulation parameters such as amplitude, frequency, duty cycle and polarity. The parameter sets include at least one adjustable stimulation parameter such as amplitude or frequency. At 631, it is determined whether the test neural stimulation provides a desired physiologic response, such as may be determined using sensors to monitor for the expected or desired response. Examples include sensing heart rate, blood pressure, respiration, laryngeal vibrations, or various combinations thereof in response to efferent vagal stimulation. If the desired physiologic response is not realized by the test neural stimulation, the process proceeds to 632 to adjust at least one test neural stimulation parameter, such as amplitude, frequency, duty cycle, and the like, and the test neural stimulation is delivered again at 630 with the revised test neural stimulation parameters. If the desired physiologic response is realized, the process proceeds from 631 to 633 to use the current test neural stimulation parameters to determine the treatment parameters for the unidirectional afferent stimulation. In some embodiments, the same parameters are used to stimulate the target nerve, except that the stimulation is applied in a manner to provide unidirectional afferent stimulation (such as swapping at least some of the adjustable parameters between stimulation anodes A1 and A2 to determine the treatment parameters from the test parameters). Some embodiment use a predetermined relationship between the afferent and efferent neural stimulation to derive or otherwise determine the treatment parameters for the unidirectional afferent stimulation based on the test parameters from the afferent stimulation. At 634, the unidirectional afferent stimulation treatment is delivered using the treatment parameters determined at 633. Some embodiments use the same electrode system to deliver both the test and the treatment stimulation.

Figure 7:
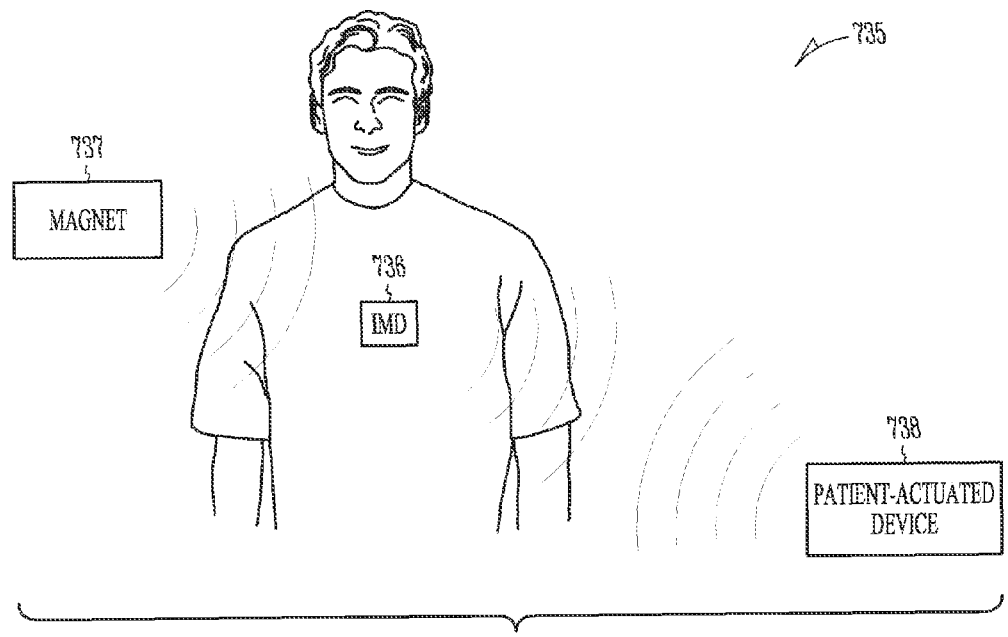
FIG. 7 illustrates an embodiment of a system with an implantable medical device (IMD).
Figure 8:
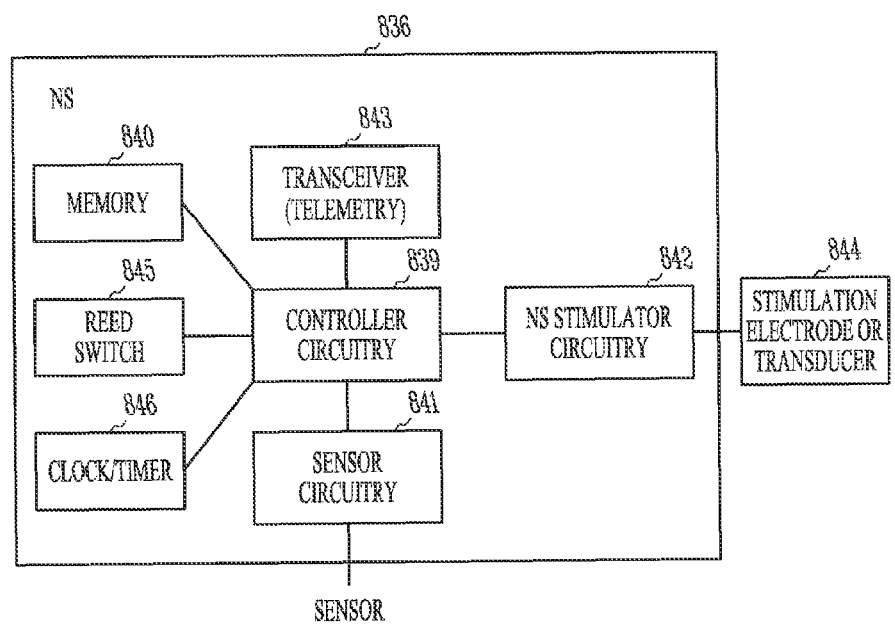
FIG. 8 illustrates an embodiment of an implantable neural stimulator (NS) device such as can be incorporated as the IMD in the system of FIG. 7.

FIG. 7 illustrates an embodiment of a system 735 with an implantable medical device (IMD) 736. The IMD is adapted to switch modes in response to a triggering event. According to various embodiments, the triggering event is an automatic event, a manually-actuated event by a patient or physician, or a combination of an automatic and manually-actuated events. Examples of automatic triggering events include a detected device change such as a detected electrode failure and a detected lead failure. Automatic triggering events can also include a detected physiologic change such as a detected change in heart rate, a detected arrhythmia, a detected change in a respiratory rate, a detected change in neural traffic, a detected change in blood pressure, and a detected change in activity. Automatic triggering events can also be based on a timer or clock, such as a device with a controller and timer adapted to follow a circadian rhythm when switching modes. Examples of manually-actuated triggers include an external magnet 737 used to actuate a switch (e.g. reed switch) in the implantable device to switch modes, and a patient-actuated external programmer 738 that enables the patient to selectively choose the mode to which the device should switch.

The programmer, capable of providing all programming functions, including mode switching, can also be used to communicate with the IMD. A manually-actuated device can be a stand-alone device designed to only provide the desired mode switching capabilities, or can be integrated into other devices. An example of a patient-actuated device includes a personal digital assistant or other electronic device such as would be used in an advanced patient management (APM)

system, which can organize and perform calculations based on recorded data, and later provide the data to a programmer.

illustrates an embodiment of an implantable neural stimulator (NS) device 836 such as can be incorporated as the IMD 736 in the system 735 of FIG. 7. The illustrated neural stimulator 836 includes controller circuitry 839 connected to a memory 840, sensor circuitry 841, neural stimulation circuitry 842, and a transceiver 843. An electrode system 844 is connected to the stimulator circuitry 842 via a port. Other means for stimulation a nerve unidirectionally may be used. For example, neural stimulation has been proposed using ultrasound, light, and thermal transducers. The memory includes instructions or algorithms operated on by the controller and further includes parameters for use in the algorithms to provide the desired neural stimulation therapy. These instructions and parameters cooperate to operate the device in a mode. The device can be operated in different modes by operating on different instructions and/or parameters. Some embodiments use the sensor, such as a neural sensor or other physiologic sensor like a heart rate sensor, to provide feedback for the neural stimulation. The stimulator circuitry is adapted to adjust parameters of the neural stimulation signal transmitted to the electrode. According to various embodiments, one or more of the amplitude, the frequency, the morphology and the burst timing (frequency and duration of bursts) are capable of being adjusted. A magnetic-actuated switch 845, such as a reed switch, is connected to the controller for use to receive a user-provided trigger (e.g. flux from the external magnet) to switch modes. Modes can be switched via communications received through the transceiver 843 from the external device or can be automatically switched, such as if mode changes are based on a clock 846 or other feedback. Historical data for mode switching can be saved in memory 840. The external device can access the memory to display the data regarding the switching events, or can otherwise process the data for a variety of purposes.

Figure 9:
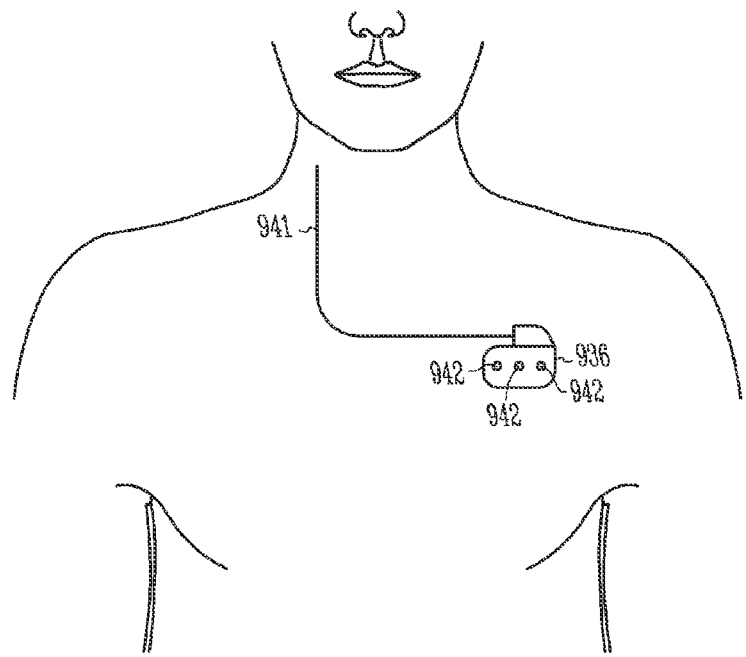
FIG. 9 illustrates a system embodiment in which an implantable medical device (IMD) is placed subcutaneously or submuscularly in a patient's chest with lead(s) positioned to stimulate a neural target in the cervical region (e.g. a vagus nerve).

FIG. 9 illustrates a system embodiment in which an implantable medical device (IMD) 936 is placed subcutaneously or submuscularly in a patient's chest with lead(s) 941 positioned to stimulate a neural target in the cervical region (e.g. a vagus nerve). The illustrated system provide a lead to the right vagus nerve. The lead could be routed to the left vagus nerve. Some embodiments use leads to stimulate both the left and right vagus nerve. According to various embodiments, neural stimulation lead(s) 941 are subcutaneously tunneled to a neural target, and can have a nerve cuff electrode to stimulate the neural target. Some vagus nerve stimulation lead embodiments are intravascularly fed into a vessel proximate to the neural target, and use electrode(s) within the vessel to transvascularly stimulate the neural target. For example, some embodiments stimulate the vagus using electrode(s) positioned within the internal jugular vein. The neural targets can be stimulated using other energy waveforms, such as ultrasound and light energy waveforms. The illustrated system includes leadless ECG electrodes on the housing of the device. These ECG electrodes 942 are capable of being used to detect heart rate, for example.

Figure 10:
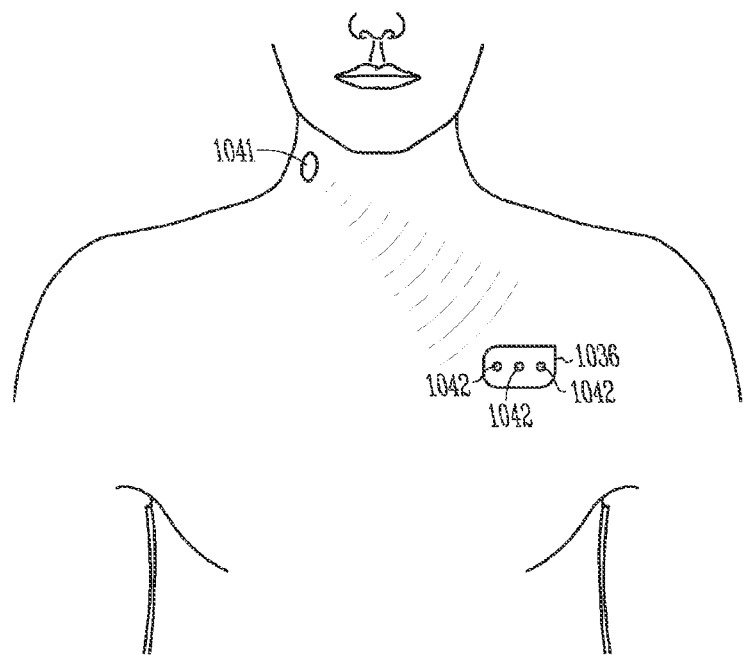
FIG. 10 illustrates a system embodiment that includes an implantable medical device (IMD) with satellite electrode(s) positioned to stimulate at least one cervical neural target (e.g. vagus nerve).

FIG. 10 illustrates a system embodiment that includes an implantable medical device (IMD) 1036 with satellite electrode(s) 1041 positioned to stimulate at least one cervical neural target (e.g. vagus nerve). The satellite electrode(s) are connected to the IMD, which functions as the planet for the satellites, via a wireless link. Stimulation and communication can be performed through the wireless link. Examples of wireless links include RF links and ultrasound links. Examples of satellite electrodes include subcutaneous electrodes, nerve cuff electrodes and intravascular electrodes. Various embodiments include satellite neural stimulation transducers used to generate neural stimulation waveforms such as ultrasound and light waveforms. The illustrated system includes leadless ECG electrodes on the housing of the device. These ECG electrodes 1042 are capable of being used to detect heart rate, for example.

Figure 11:
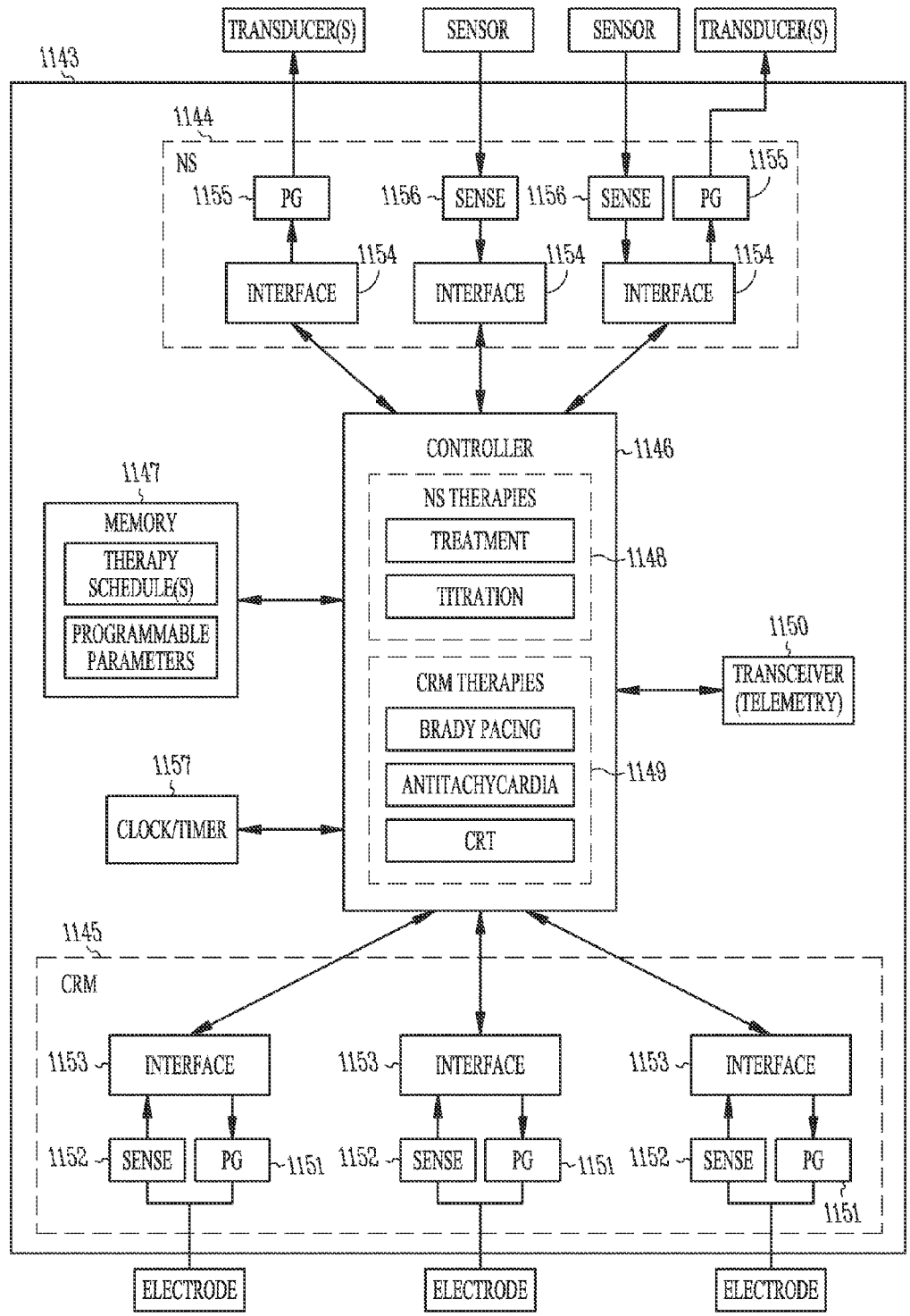
FIG. 11 illustrates an implantable medical device (IMD) having a neural stimulation (NS) component and a cardiac rhythm management (CRM) component according to various embodiments of the present subject matter.

FIG. 11 illustrates an implantable medical device (IMD) 1143 having a neural stimulation (NS) component 1144 and a cardiac rhythm management (CRM) component 1145 according to various embodiments of the present subject matter. The illustrated device includes a controller 1146 and memory 1147. According to various embodiments, the controller includes hardware, software, or a combination of hardware and software to perform the neural stimulation and CRM functions. For example, the programmed therapy applications discussed in this disclosure are capable of being stored as computer-readable instructions embodied in memory and executed by a processor. For example, therapy schedule(s) and programmable parameters can be stored in memory. According to various embodiments, the controller includes a processor to execute instructions embedded in memory to perform the neural stimulation and CRM functions. The illustrated neural stimulation therapy 1148 includes a neural stimulation treatment that includes unidirectional afferent neural stimulation for heart failure, remodeling, hypertension and others. The illustrated neural stimulation therapy 1148 further includes a titration mode used to verify the integrity of the neural stimulation delivery system and/or titrate the intensity of the neural stimulation treatment. Various embodiments include CRM therapies 1149, such as bradycardia pacing, anti-tachycardia therapies such as ATP, defibrillation and cardioversion, and cardiac resynchronization therapy (CRT). The illustrated device further includes a transceiver 1150 and associated circuitry for use to communicate with a programmer or another external or internal device. Various embodiments include a telemetry coil.

The CRM therapy section 1145 includes components, under the control of the controller, to stimulate a heart and/or sense cardiac signals using one or more electrodes. The illustrated CRM therapy section includes a pulse generator 1151 for use to provide an electrical signal through an electrode to stimulate a heart, and further includes sense circuitry 1152 to detect and process sensed cardiac signals. An interface 1153 is generally illustrated for use to communicate between the controller 1146 and the pulse generator 1151 and sense circuitry 1152. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 1144 includes components, under the control of the controller, to stimulate a neural stimulation target and/or sense parameters associated with nerve activity or surrogates of nerve activity such as heart rate, blood pressure and respiration. Three interfaces 1154 are illustrated for use to provide neural stimulation. However, the present subject matter is not limited to a particular number interfaces, or to any particular stimulating or sensing functions. Pulse generators 1155 are used to provide electrical pulses to transducer or transducers for use to stimulate a neural stimulation target. According to various embodiments, the pulse generator includes circuitry to set, and in some embodiments change, the amplitude of the stimulation pulse, the frequency of the stimulation pulse, the burst frequency of the pulse, and the morphology of the pulse such as a square wave, triangle wave, sinusoidal wave, and waves with desired harmonic components to mimic white noise or other signals. Sense circuits 1156 are used to detect and process signals from a sensor, such as a sensor of nerve activity, heart rate, blood pressure, respiration, and the like. The interfaces 1154 are generally illustrated for use to communicate between the controller 1146 and the pulse generator 1155 and sense circuitry 1156. Each interface, for example, may be used to control a separate lead. Various embodiments of the NS therapy section only includes a pulse generator to stimulate a neural target. The illustrated device further includes a clock/timer 1157, which can be used to deliver the programmed therapy according to a programmed stimulation protocol and/or schedule.

Figure 12:
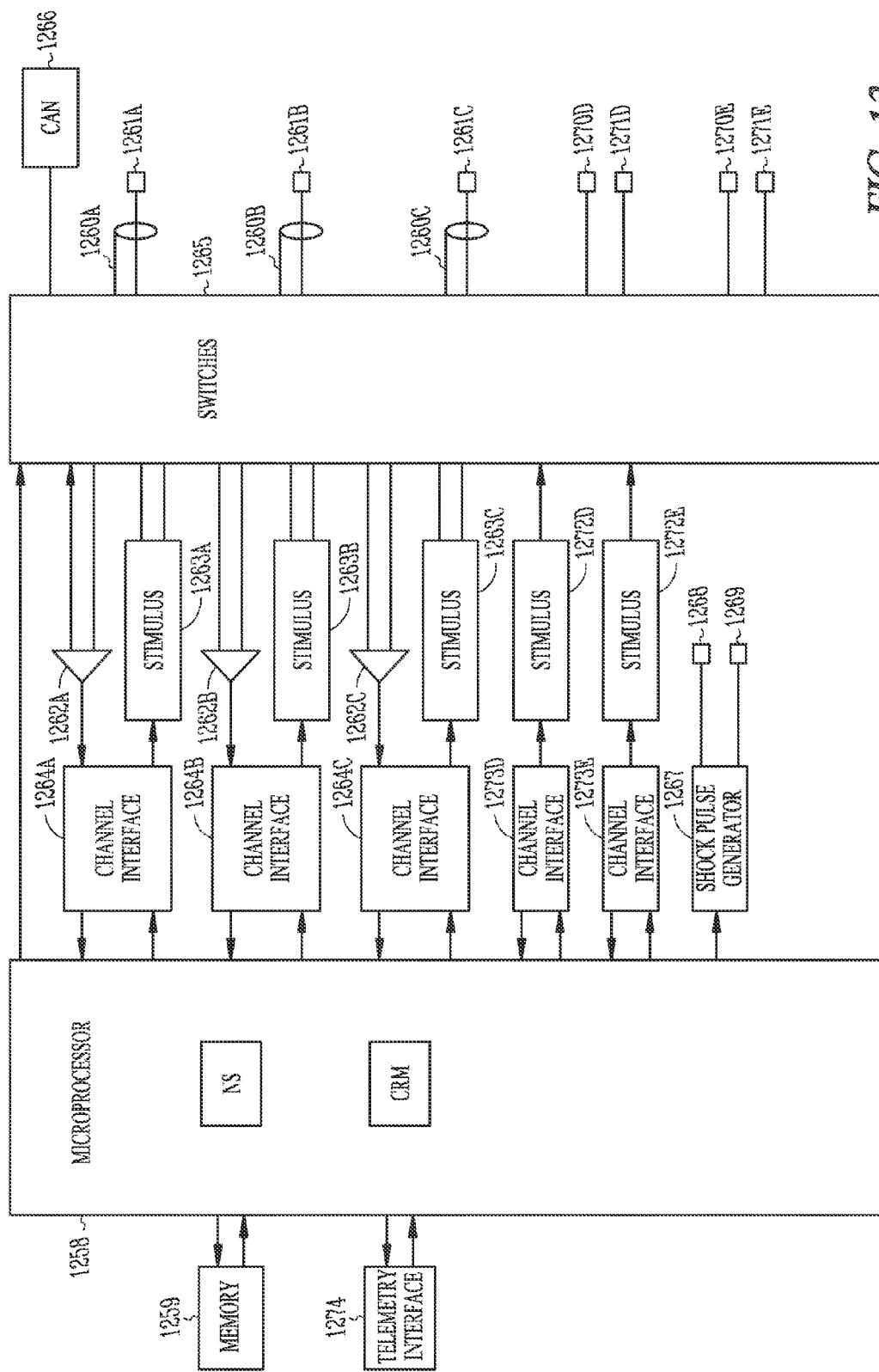
FIG. 12 shows a system diagram of an embodiment of a microprocessor-based implantable device, according to various embodiments.

FIG. 12 shows a system diagram of an embodiment of a microprocessor-based implantable device, according to various embodiments. The controller of the device is a microprocessor 1258 which communicates with a memory 1259 via a bidirectional data bus. The controller could be implemented by other types of logic circuitry (e.g., discrete components or programmable logic arrays) using astute machine type of design. Ns used herein, the term "circuitry" should be taken to refer to either discrete logic circuitry or to the programming of a microprocessor. Shown in the figure are three examples of sensing and pacing channels designated "A" through "C" comprising bipolar leads with ring electrodes 1260A-C and tip electrodes 1261A-C, sensing amplifiers 1262A-C, pulse generators 1263A-C, and channel interfaces 1264A-C. Each channel thus includes a pacing channel made up of the pulse generator connected to the electrode and a sensing channel made up of the sense amplifier connected to the electrode. The channel interfaces 1264A-C communicate bidirectionally with the microprocessor 1258, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each bipolar lead are connected via conductors within the lead to a switching network 1265 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 1266 or an electrode on another lead serving as a ground electrode. A shock pulse generator 1267 is also interfaced to the controller for delivering a defibrillation shock via a pair of shock electrodes 1268 and 1269 upon detection of a shockable tachyarrhythmia.

Neural stimulation channels, identified as channels D and E, are incorporated into the device for delivering parasympathetic stimulation and/or sympathetic inhibition, where one channel includes a bipolar lead with a first electrode 1270D and a second electrode 1271D, a pulse generator 1272D, and a channel interface 1273D, and the other channel includes a bipolar lead with a first electrode 1270E and a second electrode 1271E, a pulse generator 1272E, and a channel interface 1273E. Other embodiments may use unipolar leads in which case the neural stimulation pulses are referenced to the can or another electrode. The pulse generator for each channel outputs a train of neural stimulation pulses which may be varied by the controller as to amplitude, frequency, duty-cycle, and the like. In some embodiments, each of the neural stimulation channels uses a lead which can be intravascularly disposed near an appropriate neural target. Other types of leads and/or electrodes may also be employed. A nerve cuff electrode may be used in place of an intravascularly disposed electrode to provide neural stimulation. In some embodiments, the leads of the neural stimulation electrodes are replaced by wireless links. Neural stimulation electrodes 1270D, 1271D, 1270E and 1271E can be arranged in a tripolar electrode arrangement, where electrodes 1271D and 1271E form a common electrode.

The figure illustrates a telemetry interface 1274 connected to the microprocessor, which can be used to communicate with an external device. The illustrated microprocessor 1258 is capable of performing neural stimulation therapy routines and myocardial (CRM) stimulation routines. Examples of NS routines include a neural stimulation treatment that uses unidirectional afferent neural stimulation. Examples of myocardial or CRM routines include bradycardia pacing therapies, anti-tachycardia shock therapies such as cardioversion or defibrillation therapies, anti-tachycardia pacing therapies (ATP), and cardiac resynchronization therapies (CRT).

Figure 13:
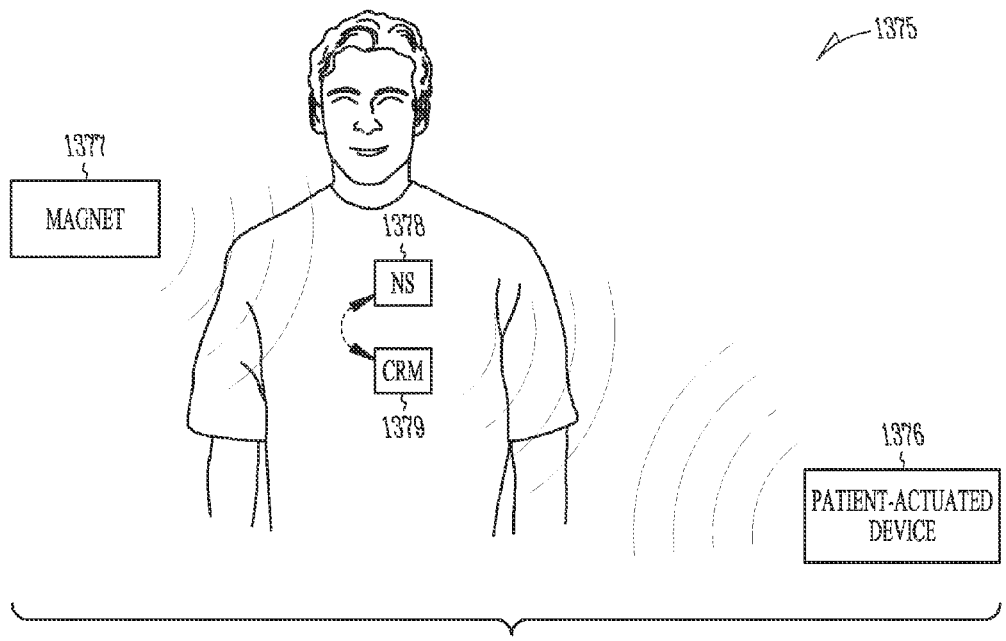
FIG. 13 illustrates a system including a manually-actuated external device, a magnet, an implantable neural stimulator (NS) device and an implantable cardiac rhythm management (CRM) device, according to various embodiments of the present subject matter.

FIG. 13 illustrates a system 1375 including a manually-actuated external device 1376, a magnet 1377, an implantable neural stimulator (NS) device 1378 and an implantable cardiac rhythm management (CRM) device 1379, according to various embodiments of the present subject matter. The NS device and the CRM device can communicate to allow one of the devices to deliver more appropriate therapy (i.e. more appropriate NS therapy or CRM therapy) based on data and/or communication signals received from the other device. Some embodiments provide on-demand communications. The illustrated NS device and the CRM device are capable of wirelessly communicating with each other, and the programmer is capable of wirelessly communicating with at least one of the NS and the CRM devices. For example, various embodiments use telemetry coils to wirelessly communicate data and instructions to each other. In other embodiments, communication of data and/or energy is by ultrasonic means. In some embodiments, a lead provides a hardwired communication path between the two devices.

Figure 14:
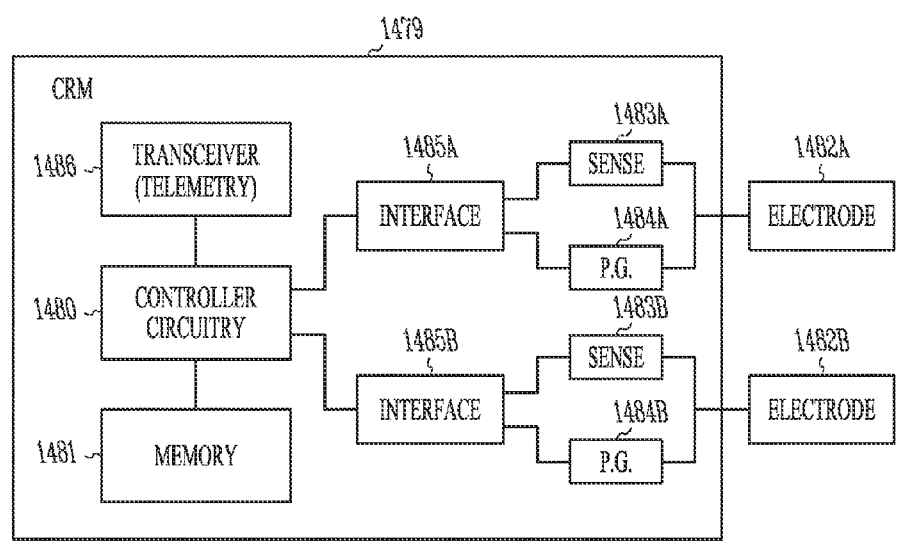
FIG. 14 illustrates an embodiment of CRM device, such as can be used in the system of FIG. 13.

FIG. 14 illustrates an embodiment of CRM device 1479, such as can be used at 1379 in the system of FIG. 13. The illustrated device 1479 includes a controller 1480 connected to a memory 1481. The figure further illustrates electrodes 1482A and 1482B connected to the device. According to the illustration, the electrodes 1482A and 1482B are connected to sense modules 1483A and 1483B to sense electrical signal at the electrode, and pulse generators 1484A and 1484B to generate stimulation signals to the electrodes. The controller 1480 is connected to the sense modules 1483A and 1483B and the pulse generator modules 1484A and 1484B via interfaces 1485A and 1485B.

The memory includes data and instructions. The controller is adapted to access and operate the instructions to perform various functions within the device, including programmed CRM therapies. The memory includes a plurality of parameters that are used to control the delivery of the therapy using a number of modes. A transceiver 1486 is connected to the controller 1480. The CRM device is capable of wireless communicating with an external device, for example, using the transceiver. For example, various embodiments use telemetry coils to wirelessly communicate data and instructions. In other embodiments, communication of data and/or energy is by ultrasonic means.

Figure 15:
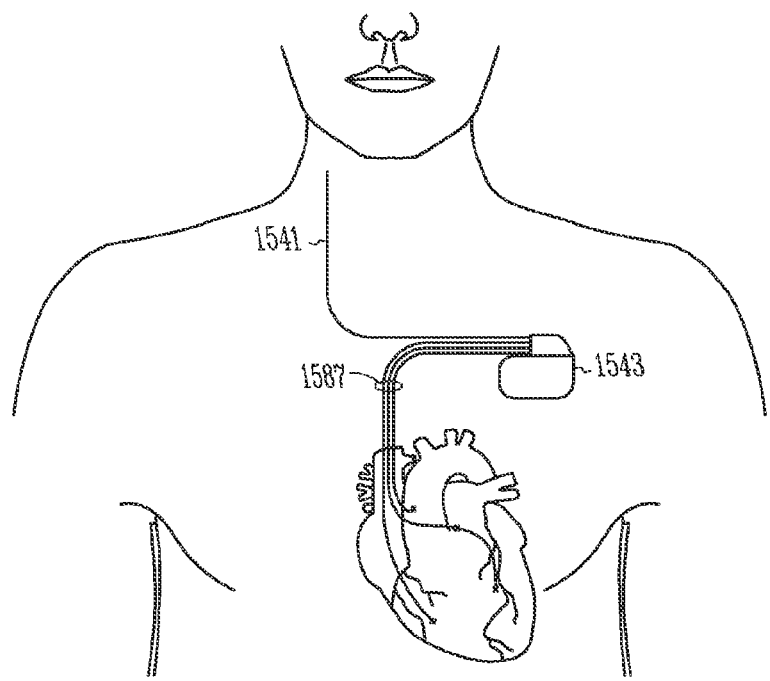
FIG. 15 illustrates an IMD placed subcutaneously or submuscularly in a patient's chest with lead(s) positioned to provide a CRM therapy to a heart, and with lead(s) positioned to stimulate and/or inhibit neural traffic at a cervical neural target to provide unidirectional neural stimulation, according to various embodiments.

FIG. 15 illustrates an IMD 1543 placed subcutaneously or submuscularly in a patient's chest with lead(s) 1587 positioned to provide a CRM therapy to a heart, and with lead(s) 1541 positioned to stimulate and/or inhibit neural traffic at a cervical neural target to provide unidirectional neural stimulation, according to various embodiments. The illustrated system provide a lead to the right vagus nerve. The lead could be routed to the left vagus nerve. Some embodiments use leads to stimulate both the left and right vagus nerve. According to various embodiments, neural stimulation lead(s) are subcutaneously tunneled to a neural target, and can have a nerve cuff electrode to stimulate the neural target. Some lead embodiments are intravascularly fed into a vessel proximate to the neural target, and use transducer(s) within the vessel to transvascularly stimulate the neural target. For example, some embodiments target the vagus nerve using electrode(s) positioned within the internal jugular vein.

Figure 16:
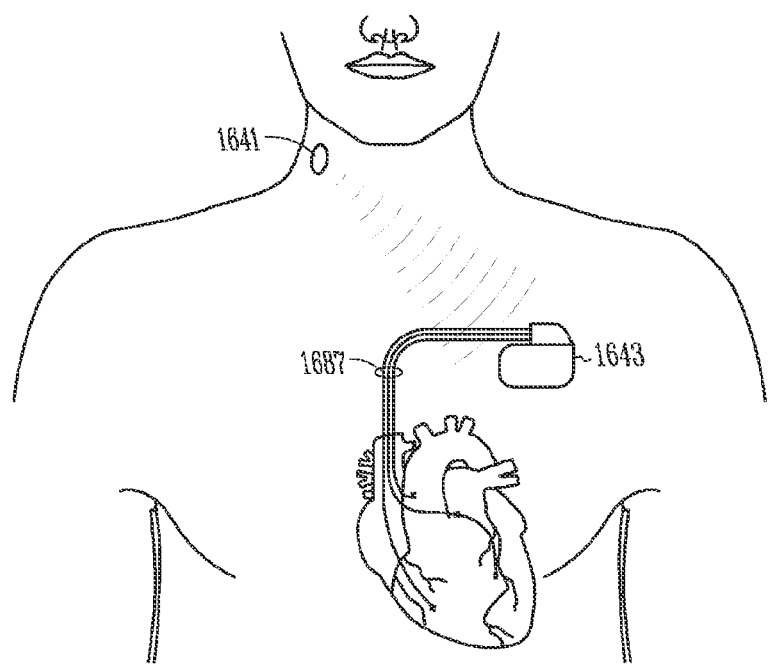
FIG. 16 illustrates an IMD with lead(s) positioned to provide a CRM therapy to a heart, and with satellite transducers positioned to stimulate/inhibit a cervical neural target to provide unidirectional neural stimulation, according to various embodiments.

FIG. 16 illustrates an IMD 1643 with lead(s) 1687 positioned to provide a CRM therapy to a heart, and with satellite transducers 1641 positioned to stimulate/inhibit a cervical neural target to provide unidirectional neural stimulation, according to various embodiments. The satellite transducers are connected to the IMD, which functions as the planet for the satellites, via a wireless link. Stimulation and communication can be performed through the wireless link. Examples of wireless links include RF links and ultrasound links. Although not illustrated, some embodiments perform myocardial stimulation using wireless links. Examples of satellite transducers include subcutaneous electrodes, nerve cuff electrodes and intravascular electrodes.

Figure 17:
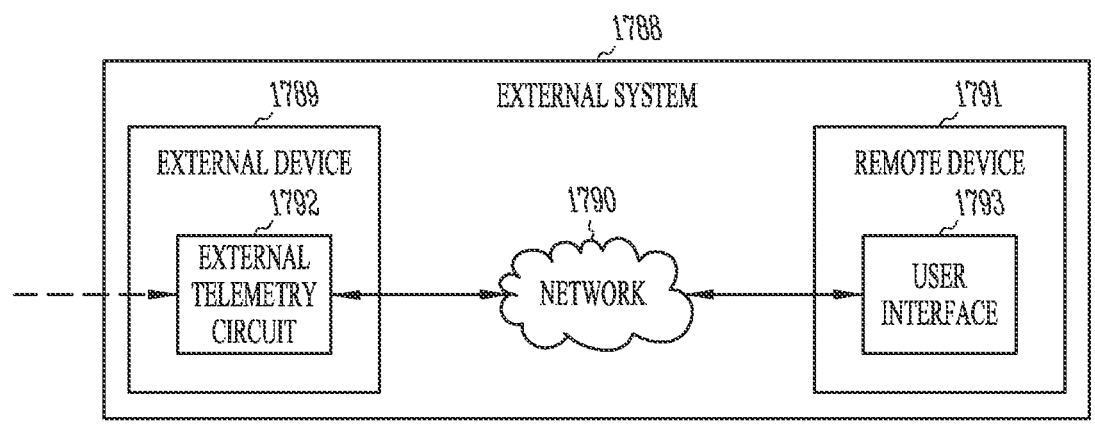
FIG. 17 is a block diagram illustrating an embodiment of an external system.

FIG. 17 is a block diagram illustrating an embodiment of an external system 1788. The external system includes a programmer, in some embodiments. In the illustrated embodiment, the external system includes a patient management system. As illustrated, the external system 1788 is a patient management system including an external device 1789, a telecommunication network 1790, and a remote device 1791. External device 1789 is placed within the vicinity of an implantable medical device (IMD) and includes external telemetry system 1792 to communicate with the IMD. Remote device(s) 1791 is in one or more remote locations and communicates with external device 1789 through network 1790, thus allowing a physician or other caregiver to monitor and treat a patient from a distant location and/or allowing access to various treatment resources from the one or more remote locations. The illustrated remote device 1791 includes a user interface 1793. According to various embodiments, the external device includes a programmer or other device such as a computer, a personal data assistant or phone. The external device 1789, in various embodiments, includes two devices adapted to communicate with each other over an appropriate communication channel, such as a computer and a Bluetooth enabled portable device (e.g. personal digital assistant, phone), by way of example and not limitation.

According to various embodiments, the device, as illustrated and described above, is adapted to deliver neural stimulation as electrical stimulation to desired neural targets, such as through one or more stimulation electrodes positioned at predetermined location(s). Other elements for delivering neural stimulation can be used. For example, some embodiments use transducers to deliver neural stimulation using other types of energy, such as ultrasound, light, magnetic or thermal energy.

One of ordinary skill in the art will understand that, the modules and other circuitry shown and described herein can be implemented using software, hardware, and combinations of software and hardware. As such, the terms module and circuitry, for example, are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods are implemented using a computer data signal embodied in a carrier wave or propagated signal, that represents a sequence of instructions which, when executed by a processor cause the processor to perform the respective method. In various embodiments, the methods are implemented as a set of instructions contained on a computer-accessible medium capable of directing a processor to perform the respective method. In various embodiments, the medium is a magnetic medium, an electronic medium, or an optical medium.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:
1. A system, comprising:
 a neural stimulator configured to generate neural stimulation signals for use in delivering neural stimulation;
 a controller connected to the neural stimulator, the controller and the neural stimulator being configured to generate a first neural stimulation signal for use in delivering unidirectional afferent neural stimulation to a target nerve for a neural stimulation therapy, and to generate a second neural stimulation signal for use in delivering efferent neural stimulation to the target nerve, wherein in delivering the efferent neural stimulation, a measurable physiologic effect is elicited by nerve traffic in an efferent direction, and wherein in delivering the unidirectional afferent neural stimulation, the measurable physiologic effect is not elicited;
 at least one sensor configured to sense a physiologic response for the measurable physiologic effect to the efferent neural stimulation of the target nerve; and
 the controller being connected to the at least one sensor, the controller being configured to compare a sensed physiologic response to the efferent neural stimulation to a desired physiologic response, and adjust at least one efferent neural stimulation parameter for the second neural stimulation signal for use in delivering efferent neural stimulation that results in the desired physiologic response, the controller further being configured to deliver the unidirectional afferent neural stimulation using afferent neural stimulation parameters determined using the at least one efferent neural stimulation parameter that provided the desired physiologic response.

2. The system of claim 1, wherein the controller is configured to generate the second neural stimulation signal for use in delivering unidirectional efferent neural stimulation to the target nerve to provide the measurable physiologic effect.

3. The system of claim 1, wherein the controller is configured to generate the second neural stimulation signal for use in delivering a general efferent neural stimulation to the target nerve to provide the measurable physiologic effect.

4. The system of claim 1, wherein the neural stimulator is configured to generate neural stimulation signals for use in delivering neural stimulation using a tripolar electrode.

5. The system of claim 4, wherein:
in generating the second neural stimulation signal, the controller is configured to use the tripolar electrode to deliver a unidirectional efferent neural stimulation to the target nerve to elicit nerve traffic in the efferent direction;
the tripolar electrode includes a cathode, a first anode and a second anode; and
the controller is configured to adjust the stimulation patterns such that a first anodal current associated with the first anode during the unidirectional efferent stimulation is approximately the second anodal current associated with the second anode during the unidirectional afferent stimulation, and the second anodal current associated with the second anode during the unidirectional efferent stimulation is approximately the first anodal current associated with the first anode during the unidirectional afferent stimulation.

6. The system of claim 1, wherein the controller and the neural stimulator are configured to generate the first neural stimulation signal for use in delivering unidirectional afferent neural stimulation to a vagus nerve, and to generate a second neural stimulation signal fir use in delivering efferent neural stimulation to the vagus nerve.

7. The system of claim 6, wherein the controller and the neural stimulator are configured to generate a first test neural stimulation signal for use in delivering unidirectional afferent neural stimulation to a left vagus nerve and a second test neural stimulation signal for use in delivering unidirectional afferent stimulation to a right vagus nerve, and to generate a first treatment neural stimulation signal for use in delivering efferent neural stimulation to the left vagus nerve and a second treatment neural stimulation signal for use in delivering efferent neural stimulation to the right vagus nerve.

8. The system of claim 1, wherein the controller is configured to interrupt delivering unidirectional afferent neural stimulation to the target nerve to deliver efferent neural stimulation.

9. The system of claim 1, wherein the controller is configured to automatically interrupt delivering unidirectional afferent neural stimulation according to a schedule.

10. The system of claim 1, wherein the controller is configured to automatically interrupt delivering unidirectional afferent neural stimulation in response to a device event.

11. The system of claim 1, wherein the controller is configured to interrupt delivering unidirectional afferent neural stimulation in response to a manually-initiated command.

12. The system of claim 1, wherein the at least one sensor includes a blood pressure sensor.

13. The system of claim 1, wherein the at least one sensor includes a heart rate sensor.

14. The system of claim 1, wherein the at least one sensor includes a laryngeal vibration sensor.

15. A system, comprising:
a neural stimulator configured to generate neural stimulation signals for use in delivering neural stimulation using a tripolar electrode;
a controller connected to the neural stimulator, the controller and the neural stimulator being configured to generate a first neural stimulation signal for use in delivering unidirectional afferent neural stimulation to a target nerve for a neural stimulation therapy, and to generate a second neural stimulation signal for use in delivering efferent neural stimulation to the target nerve, wherein in delivering the efferent neural stimulation, a measurable physiologic effect is elicited by nerve traffic an efferent direction, and wherein in delivering the unidirectional afferent neural stimulation, the measurable physiologic effect is not elicited;
at least one sensor configured to sense a physiologic response for the measurable physiologic effect to the efferent neural stimulation of the target nerve;
the controller being connected to the at least one sensor, the controller being configured to compare a sensed physiologic response to the efferent neural stimulation to a desired physiologic response, and adjust at least one efferent neural stimulation parameter for the second neural stimulation signal for use in delivering efferent neural stimulation that results in the desired physiologic response, the controller further being configured to deliver the unidirectional afferent neural stimulation using afferent neural stimulation parameters determined using the at least one efferent neural stimulation parameter that provided the desired physiologic response,
wherein the controller and the neural stimulator are configured to generate the first neural stimulation signal for use in delivering unidirectional afferent neural stimulation to a vagus nerve, and to generate a second neural stimulation signal for use in delivering efferent neural stimulation to the vagus nerve.

16. The system of claim 15, wherein the controller is configured to implement a schedule to automatically interrupt delivering unidirectional afferent neural stimulation to the target nerve to deliver efferent neural stimulation.

17. The system of claim 15, wherein the controller is configured to respond to a device event, wherein in response to the device event the controller is configured to automatically interrupt delivering unidirectional afferent neural stimulation to the target nerve to deliver efferent neural stimulation.

18. The system of claim 15, wherein the controller is configured to respond to a manually-initiated command, wherein in response to the manually-initiated command, the controller is configured interrupt delivering unidirectional afferent neural stimulation to the target nerve to deliver efferent neural stimulation.

19. The system of claim 15, wherein the controller is configured to generate the second neural stimulation signal for use in delivering unidirectional efferent neural stimulation to the target nerve to provide the measurable physiologic effect.

20. The system of claim 15, wherein the controller is configured to generate the second neural stimulation signal for use in delivering a general efferent neural stimulation to the target nerve to provide the measurable physiologic effect.

* * * * *